(12) United States Patent
Harvey et al.

(10) Patent No.: US 8,357,335 B1
(45) Date of Patent: Jan. 22, 2013

(54) COLORIMETRIC ASSAY FOR THE DETERMINATION OF HYDROLYSIS ACTIVITY FROM HD AND OTHER HALOGENATED ORGANICS

(75) Inventors: Steven P. Harvey, Fallston, MD (US); Joseph J. DeFrank, Bel Air, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 1635 days.

(21) Appl. No.: 11/272,422

(22) Filed: Nov. 9, 2005

(51) Int. Cl.
*G01N 33/00* (2006.01)
(52) U.S. Cl. .......... 422/401; 422/50; 422/561; 436/104; 436/165; 435/262.5; 588/405
(58) Field of Classification Search ............... 422/401, 422/561, 50; 436/104, 165; 435/262.5, 264; 588/405
See application file for complete search history.

(56) References Cited

U.S. PATENT DOCUMENTS 6,017,750 A * 1/2000 Harvey et al. .............. 435/262.5

* cited by examiner

*Primary Examiner* — Lyle Alexander
(74) *Attorney, Agent, or Firm* — Ulysses John Biffoni

(57) ABSTRACT

An assay for screening potential hydrolysis enhancing agents capable of facilitating the hydrolysis of a substantially water insoluble halogenated compound such as mustard gas (HD) in an aqueous reaction mixture is disclosed. The assay includes at least one chamber adapted for receiving and retaining the substantially water insoluble mustard gas compound and a potential hydrolysis agent in an aqueous reaction mixture, and a pH indicating agent adapted to produce a visible color change corresponding to the amount of the substantially water insoluble mustard gas compound hydrolyzed in the aqueous reaction mixture wherein the rate of hydrolysis can be established by measuring the change in the detectable signal over time.

15 Claims, 4 Drawing Sheets
(2 of 4 Drawing Sheet(s) Filed in Color)

COLORIMETRIC ASSAY FOR THE DETERMINATION OF HYDROLYSIS ACTIVITY FROM HD AND OTHER HALOGENATED ORGANICS

GOVERNMENT INTEREST

The invention described herein may be manufactured, used and licensed by or for the U.S. Government.

FIELD OF THE INVENTION

The present invention relates to chemical reaction assays, and more particularly to an assay for screening potential hydrolysis-enhancing agents capable of enhancing the hydrolysis of water-insoluble halogenated compounds including chemical warfare agents such as sulfur mustard (HD), in an aqueous environment.

BACKGROUND OF THE INVENTION

Many halogenated compounds including chemical warfare agents such as HD can be decontaminated into a less toxic form via oxidation reactions through the use of, for example, aqueous bleach or via substitution reactions through the use of, for example, aqueous alkali, organic alkali, basic hydrogen peroxide, or monoethanolamine. Typically, such decontamination reactants exhibit desirable rapid reaction rates and broad range reactivity. However, they often are limited in terms of material incompatibility. In addition, they usually require large quantities to achieve acceptable results, which can impose serious logistical burdens.

Oxidizing reactants offer a particularly broad-spectrum approach to decontamination. However, oxidizing reactants exhibit unpredictable chemical stability. Moreover, the logistics needed to handle and administer such oxidizing reactants are often problematic due to the typically unfavorable stoichiometry. Some oxidation/substitution reactions have also been shown to be effective against biological agents; there are others that may be effective but remain untested.

Hydrolysis reactions can be effective in decontamination, and offer their own unique advantages including substantially more favorable stoichiometry (one or two water molecules react with one agent molecule of about 10 times greater mass) and the nearly widespread availability of water. Hydrolysis can be used to decontaminate or break down HD also known as mustard gas (sulfur mustard, 2,2'-dichlorodiethyl sulfide) to yield thiodiglycol (TDG). The difference in toxicity between HD and TDG is a factor of 4,200 to 5,700 (the oral LD50 of HD is 0.7 mg/kg whereas that of TDG is 3000-4000 mg/kg). This large reduction in toxicity offers the potential to seriously reduce the damage caused by HD if it can be decontaminated in a rapid manner. The hydrolysis reaction of HD is shown in Scheme 1 below.

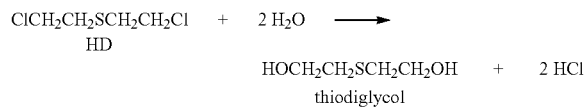

Scheme 1

$ClCH_2CH_2SCH_2CH_2Cl + 2 H_2O \longrightarrow$
HD
$HOCH_2CH_2SCH_2CH_2OH + 2 HCl$
thiodiglycol For purposes of decontamination, the HD hydrolysis reaction offers the important advantage of yielding a product (thiodiglycol, 2,2'-thiodiethanol) that is water soluble, biodegradable, and of very low toxicity (approximately 5,000 times less toxid than HD). However, the direct reaction between HD and water is too slow to use for decontamination under ambient conditions.

The rates of hydrolysis reactions are generally low in comparison to oxidation reactions. Such reactions including HD hydrolysis reactions can be accelerated significantly with the use of hydrolysis-enhancing agents such as catalysts and surfactants. In particular, such catalysts including enzymes can dramatically increase the rate of reaction by lowering the activation energy of the reaction pathway. However, catalysts exhibit a relatively narrow specificity of activity, where significant activity differences can be observed between even two stereoisomers of the same compound.

Decontamination reactions using catalytic enzymes are well characterized. In the decontamination of G-type organophosphate chemical nerve agents, they have been used for a range of G-type substrates. For example, organophosphate hydrolase (OPH) enzymes have been shown to catalyze and enhance the hydrolysis of the P-S bond in V-type phosphonothiolate agents.

Hydrolytic dehalogenase enzymes have been found to possess dehalogenase activity against HD upon dissolving the HD compound in alcohol, and then adding the resulting mixture to the enzymes in an aqueous reaction matrix. In the absence of alcohol, neat HD is substantially insoluble in water and the HD molecules would be inaccessible to the enzymes. In this manner, the use of surfactants or compounds that increase the water solubility or dispersion of HD in the aqueous matrix can be used to further enhance and accelerate the rate of reaction. Thus, the search and selection of suitable hydrolysis enhancing agents including surfactants, phase transfers catalysts, enzymes and the like, would greatly aid the rapid decontamination of water insoluble chemical warfare agents such as HD. The reactivity of other halogenated compounds could be similarly accelerated.

Such search is tedious and time-consuming. The determination of the hydrolysis rate of HD and other halogenated compounds is technically problematic, due largely in part to the heterogenous nature of the reaction between water and such compounds. The aqueous-insoluble HD undergoes an interfacial reaction with the surrounding water molecules. The rate of the mass-transfer limited reaction is difficult to measure in a reproducible manner because small and essentially random differences in the physical conformation of the HD droplets in the reaction can cause large differences in the overall hydrolysis rate.

There are several means available to measure or estimate the HD hydrolysis rate. For instance, the rate can be measured using a chloride electrode to monitor the rate of chloride release as the HD undergoes hydrolysis. Alternatively, the biphasic reaction can be extracted with an organic solvent from which the residual HD can be analyzed by chromatography. Prior to the availability of modern chromatographic instruments, the overall time of reaction was measured by the visual disappearance of the organic HD layer from the reaction. Such approaches have inherently large variability caused by the variations in the size and shape of the hydrophobic mustard droplets in the reaction. Even under conditions of well controlled agitation, the physical properties of HD cause it to disperse in a highly variable manner. In addition, these assays are relatively labor intensive and time consuming, and frequently require the use of expensive instruments. Particularly within the confines of a high containment laboratory, these limitations are very significant.

For this reason, it would be useful to rapidly and inexpensively screen for potentially useful compounds that enhance the hydrolysis of chemical warfare agents such as HD. Such compounds would be selected based on their capacity to increase the rate of reaction and/or enhance solubility and contact of chemical warfare agents in an aqueous matrix. There is a need to develop a practical means of accurately testing to visually compare hydrolysis rates of various compounds in the presence of the chemical warfare agent in a consistent, reliable manner.

SUMMARY OF THE INVENTION

The present invention relates generally to an assay for screening potential hydrolysis enhancing agent capable of enhancing the hydrolysis of relatively water insoluble compounds including chemical warfare agents such as HD in an aqueous environment or matrix. The assay of the present invention permits potential hydrolysis enhancing agents to be tested under the same conditions, while providing a convenient way to visually determine the relative hydrolysis rates of a chemical warfare agent such as HD in a reliable and reproducible manner. Such potential hydrolysis enhancing agents may include surfactants and catalysts that enhance the rate of hydrolysis through increased aqueous solubility and/or reduction in the activation energy of the reaction. The present invention reduces the cost, time and labor associated with testing such compounds, while maintaining good accuracy, reliability and reproducibility.

Previous aqueous studies using HD pre-dissolved in isopropanol have shown that the effectiveness of HD enzymatic degradation is a function of the homogeneity of the HD-water system. In the present invention, a microtiter plate assay was developed for the purpose of screening a series of compounds with the potential to increase the solubility or dispersion of HD in an aqueous matrix. The assay used meta-cresol purple dye as a pH indicator in a series of buffer concentrations to monitor the acid produced from HD hydrolysis. The extent of hydrolysis could be observed colorimetrically in a time-controlled series of reactions that allowed simultaneous comparison of numerous compounds or conditions on a single microtiter plate.

Sixty-seven different detergents, surfactants, or different concentrations thereof were screened to determine their effect on HD hydrolysis rate. All were observed to inhibit HD hydrolysis. The results observed indicate that the micelles did not function in a manner to increase the interaction between the hydrophobic HD and the surrounding water.

In one aspect of the present invention, there is provided an assay for screening potential hydrolysis enhancing agents capable of enhancing the hydrolysis of a substantially water insoluble compound in an aqueous reaction mixture, the assay comprising:

at least one chamber adapted for receiving and retaining the substantially water insoluble compound and a potential hydrolysis agent in an aqueous reaction mixture; and an indicating agent adapted to produce a detectable signal corresponding to the amount of the substantially water insoluble compound hydrolyzed in the aqueous reaction mixture, wherein the rate of hydrolysis can be established by measuring the change in the detectable signal over time.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings are illustrative of embodiments of the present invention and are not intended to limit the invention as encompassed by the claims forming part of the application.

DETAILED DESCRIPTION OF THE INVENTION

The present invention is directed to an assay for screening potential hydrolysis enhancing agent for facilitating the hydrolysis of water insoluble chemical warfare agents including HD in an aqueous environment or matrix. The assay of the present invention enables the potential hydrolysis enhancing agents to be tested under the same conditions to provide a convenient means to visually determine the relative hydrolysis rates of a chemical warfare agent such as HD in a reliable and reproducible manner. Such potential hydrolysis enhancing agents may include surfactants and catalysts that enhance the rate of hydrolysis through increase aqueous solubility and/or marked reduction in the activation energy of the reaction.

The assay of the present invention is efficient and highly reliable. It is capable of screening and selecting prospective hydrolysis enhancing agents in a time- and labor efficient manner for purposes of decontamination of chemical warfare agents without the need to use expensive analytical equipment. The present assay further operates in a manner to quickly eliminate poor candidates. In one embodiment of the present invention, the present assay allows rapid testing of materials that may facilitate HD aqueous solubility, and enhance the rate of hydrolysis of the HD compound for rapid decontamination.

As used herein, the term "hydrolysis enhancing agent" encompasses any compound that is capable of enhancing the hydrolytic degradation of substantially water insoluble compounds including, for example, water insoluble halogenated compounds including chemical warfare agents such as, for example, HD (mustard gas). Water insoluble compounds that can be hydrolyzed are generally difficult to react in an aqueous reaction mixture, and thus require the presence of some form of hydrolysis enhancing agent. Such hydrolysis enhancing agents can be selected from catalysts, enzymes, surfactants, detergents and combinations thereof.

Figure 1A:
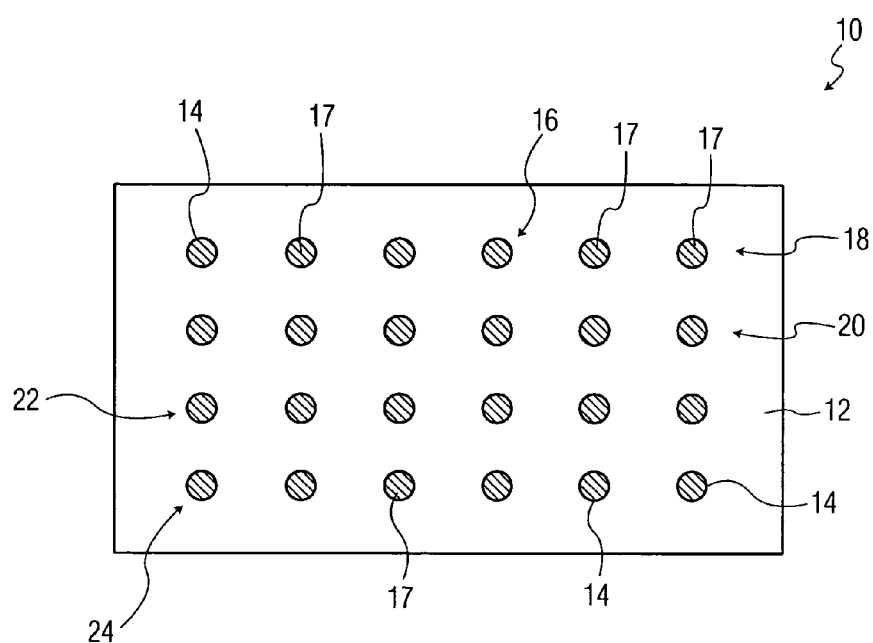
FIG. 1A is a top plan view of an assay for screening potential hydrolysis enhancing agents capable of facilitating the hydrolysis of a substantially water insoluble compound in an aqueous reaction mixture for one embodiment of the present invention.

Referring to FIG. 1A, a colorimetric assay support 10 is shown for one embodiment of the present invention. The assay support 10 includes a tray or well plate 12 defining multiple reaction chambers or wells 14 arranged in an array 16 of first, second, third and fourth rows 18, 20, 22, and 24, respectively. The reaction chambers 14 of the tray 12 are configured to receive and retain an aqueous reaction mixture 17 for implementing the assay of the present invention. The assay support 10 is used to test one or more potential hydrolysis enhancing agents for any activity associated with enhancing the hydrolytic reaction of the substantially water insoluble compound. In this embodiment, the assay support 10 is used to test one potential hydrolysis enhancing agent on the substantially water insoluble compound.

The aqueous reaction mixture 17 is formulated to contain a detectable indicating agent such as a pH indicator. In the present embodiment, the pH indicator is meta-cresol purple. The aqueous reaction mixtures 17 retained in successive chambers 14 of each respective row 18, 20, 22, and 24, are further formulated to contain graduated concentrations of a buffer. The buffer is added to resist change in pH in the aqueous reaction mixture 17 upon production of small amounts of acid or base. Examples of buffers include tris maleate buffer, 2,4,6-trimethylpyridine, Sorensen's phosphate buffer, sodium cacodylate buffer, Pipes buffer solution, 3-(N-morpholino) propanesulfonic acid, Millonig's phosphate buffer, Hepes buffer solution, citrate buffer, acetate buffer and the like.

The term "detectable indicating agent" encompasses any compound capable of producing a detectable signal corresponding to the amount of the substantially water insoluble compound hydrolyzed in the aqueous reaction mixture. An example of a suitable detectable indicating agent where the hydrolysis reaction generates $H^+$ (proton) is a pH indicator such as thymol blue, meta-cresol purple or a universal indicator. The pH indicator changes color of the aqueous reaction mixture 14 depending on the pH (acidity or alkalinity). In this manner, the amount of the reactant hydrolyzed to yield protons in the aqueous reaction mixture 14 can be readily determined.

In the first row 18, the aqueous reaction mixture 17 contains only the buffer in graduated concentrations and the pH indicator to provide a control for the assay of the present invention. In the second row 20, the aqueous reaction mixture 17 contains the buffer in graduated concentrations, the pH indicator and the water insoluble compound in the amount of about 1% by weight based on the total weight of the mixture, to establish the spontaneous or native rate of hydrolysis in the absence of the potential hydrolysis enhancing agent.

In the third row 22, the aqueous reaction mixture 17 contains the buffer in graduated concentrations, the pH indicator, and a potential hydrolysis enhancing agent to provide a control to observe pH effects from the potential hydrolysis enhancing agent. In the fourth row 24, the aqueous reaction mixture 17 is the test sample, and contains the buffer in graduated concentrations, the pH indicator, the potential hydrolysis enhancing agent, and the water insoluble compound in the amount of about 1% by weight based on the total weight of the mixture.

Once prepared, the tray 12 is placed on a microtiter plate shaker to provide uniform and consistent agitation to the aqueous reaction mixture 17. The sample can be incubated for about 30 minutes. As the water insoluble compound is hydrolyzed, acid is generated in the chambers 14 in the order of increasing buffer concentration. The pH indicator turns from purple to yellow to red from an alkaline pH to an acidic pH. The relative rates of hydrolysis can be determined by observing the number of chambers 14 in a given row 18, 20, 22, or 24 that changed color at a predetermined point in time. In this manner, a relative comparison can thus be made between the test sample row 24 and the control rows 18, 20 and 22. The row exhibiting more chambers 14 with color changes would have a greater rate of hydrolysis than a row with lesser number of chambers 14 showing a color change in a given time period.

Figure 3:
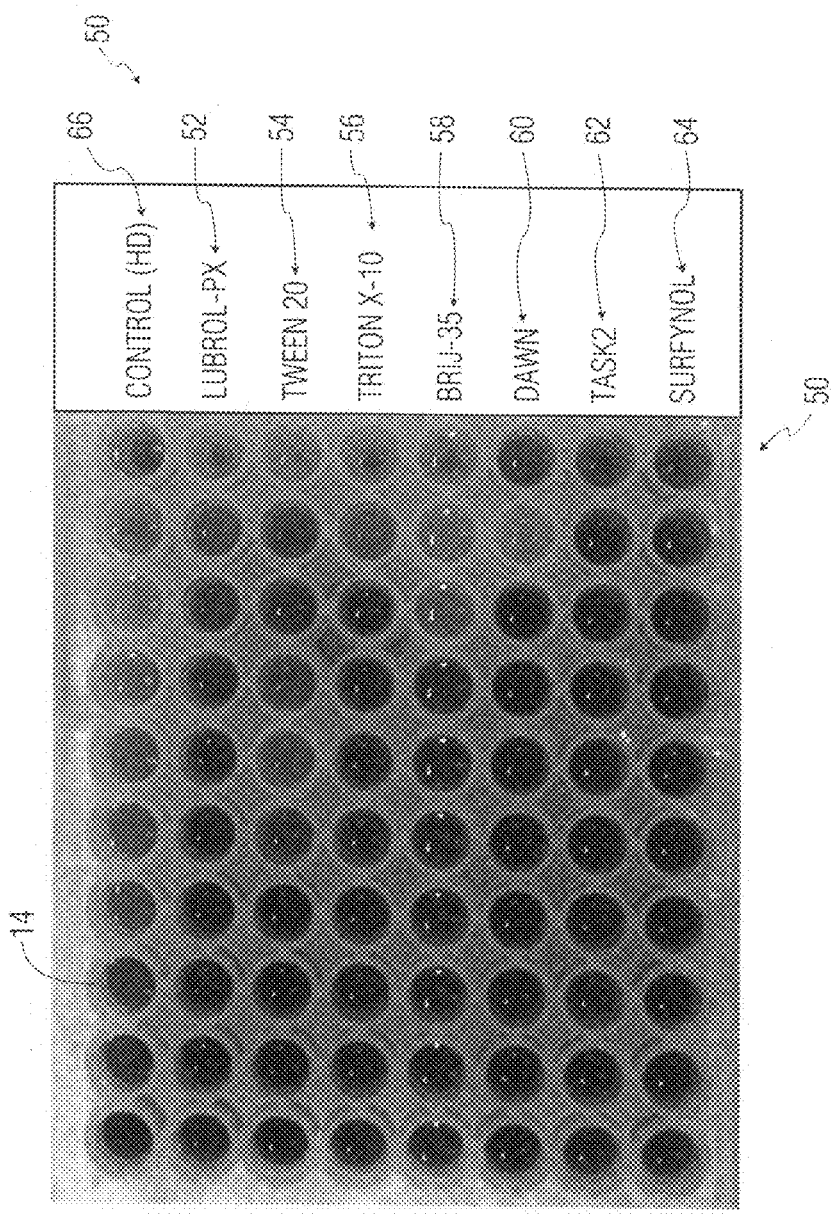
FIG. 3 is a top plan view of an assay containing a control represented by the top row of reaction chambers, and seven test compounds added at a final concentration of 1% each represented by the corresponding rows of reaction chambers in accordance with the present invention.

In another embodiment of the present invention, an assay support 50 (as shown in FIG. 3) facilitates simultaneously testing multiple samples ranging from seven to nine in a 96-well plate format. The only equipment required is a microtiter plate shaker or agitator. Reproducibility of the assays is greatly improved since all samples are incubated and agitated under the same conditions. Labor required to prepare the assay is minimal and takes about a minute per sample. Cost is also very low, primarily due to the low labor requirement and the minimal materials needed.

There are numerous ways the assays can be configured, depending on the number of desired controls and the accuracy of the measurements required. For instance, larger numbers of samples can be assayed with smaller numbers of dilutions per sample. Also, thymol blue indicator dye can be used in place of meta-cresol purple with essential similar results. The amount of HD added per well is variable although it is necessary to increase or decrease the buffer concentrations accordingly.

EXAMPLE

Materials and Methods

Samples of HD were obtained from a 1-ton storage container (Aberdeen Proving Ground, Md.). The HD samples were stabilized with tributylamine and were measured to be approximately 90% pure. Quantitative assays were conducted with a chloride electrode attached to a Fisher Accumet 925 meter. Reactions were conducted in a temperature-controlled vessel in a total volume of 5 mL. Buffering was provided by a 50 mM solution of MOPS at pH 7.2. Data logging was automated through an RS-232 connection to a computer.

The microtiter plate assays were performed solely with polypropylene plates to prevent direct HD reaction with the plate material as was previously observed with polyethylene plates. All assays were performed at room temperature and the buffer used was ammonium carbonate. Indicators were purchased from Aldrich Chemical Company, St. Louis, Mo.

Figure 1B:
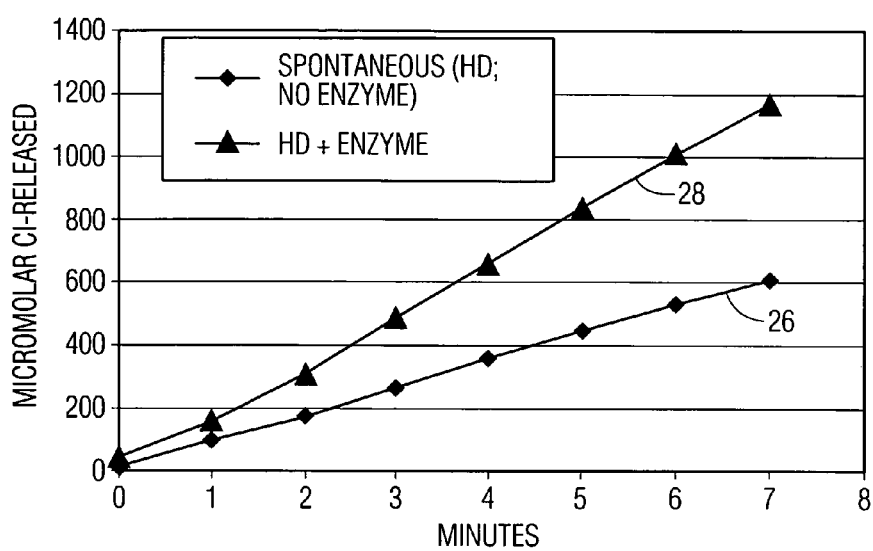
FIG. 1B is a graph depicting the rates of chloride release in a spontaneous hydrolysis reaction of HD versus enzyme catalyzed hydrolysis reaction of HD, each carried out in a reaction mixture containing 10% isopropanol and reaction buffer (50 mM MOPS buffer, pH 7.2)
Figure 2:
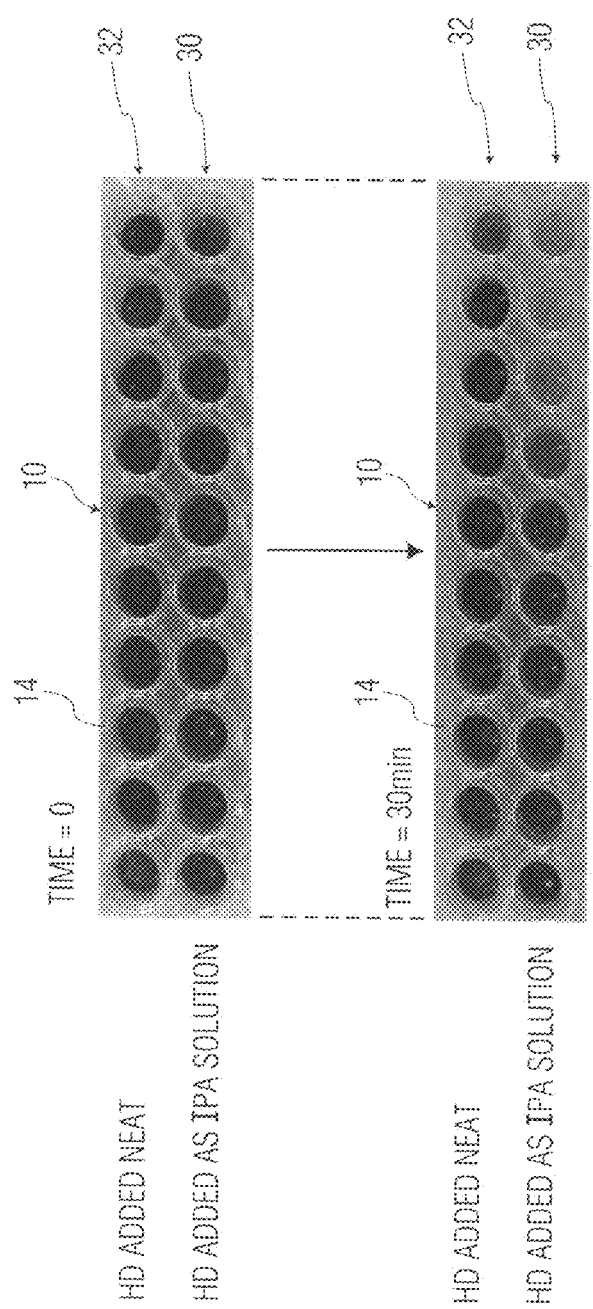
FIG. 2 are top plan views of an assay at time=0 and at time=30 minutes, respectively, to show observed visually perceptable differences in HD hydrolysis rate between neat HD and HD with 10% isopropanol solution as a positive control showing an increase in HD hydrolysis rate in accordance with the present invention.

Results and Discussion:

Enzyme-catalyzed hydrolysis of HD has been demonstrated in reactions where HD dissolved in alcohol is added to aqueous buffer. FIG. 1B shows a graph with the corresponding increase in the chloride release rate in a sample reaction. However, when the HD is added as neat to the same reaction above, there is no detectable difference in rates between the spontaneous reactions as indicated by curve 26 and enzyme-catalyzed reactions as indicated by curve 28. The spontaneous rate is also much slower in the absence of the alcohol solvent. The simplest explanation of these results is that the insoluble neat HD is poorly distributed in the aqueous buffer and is presumably relatively inaccessible to the aqueous-dissolved enzyme. This explanation is consistent with the visual observation of a relatively homogeneous reaction matrix with HD/isopropanol versus a heterogeneous matrix observed when neat HD is added to aqueous buffer.

While the chloride electrode assay is quantitative and reproducible as an assay of the HD hydrolysis rate, it permits evaluation of only a single set of conditions at a time. A plate assay, on the other hand, would offer the potential to evaluate several compounds plus controls simultaneously in a semi-quantitative manner. Such an assay could provide a powerful screening tool for the effect of various materials on the hydrolysis rate of HD.

The complete HD hydrolysis reaction proceeds through a series of sulfonium ion intermediates and yields two equivalents of HCl. The overall balanced hydrolysis reaction is illustrated in Scheme 1 above. Because HD hydrolysis is a mass-transfer limited reaction, increases in solubility or dispersion are reflected in a corresponding increase in hydrolysis rate and acid production. Many materials are known to facilitate the dissolution or dispersion of one compound in another for the purpose of facilitating chemical reactions.

A few examples include phase transfer catalysts such as quaternary ammonium compounds and quaternary phosphonium compounds, or detergents. Because there were no reports known to Applicants of compounds that facilitated the dissolution of HD in an aqueous matrix, Applicants needed to test a number of materials that might dissolve or disperse HD in aqueous buffer. Toward that end Applicants sought to develop a plate assay based on change in pH resulting from the corresponding increase in hydrolysis rate.

The decrease in pH can be followed by incorporating pH indicator dye into a series of buffer concentrations. The rate at which the hydrolysis reaction produces HCl can then potentially be tracked by observing the number of wells with color changes in a given time period. The assay was set up as follows: Ammonium carbonate buffer was prepared in a series of concentrations between 0.5 and 5.0 mg/mL in 0.5 mg/mL increments. To these dilutions, meta-cresol purple dye was added at a final concentration of 1 mg/mL (thymol blue dye was also used, with essentially similar results). The dye changes color from purple (pH 9.0) to yellow (pH 7.4) to red (pH 1.2) as pH decreases due to HCl production from HD hydrolysis.

Dye-containing buffer dilutions were then added to the plate 12 at 140 μL per well 14 in the order of buffer concentration.

Controls and Experimental Wells were as Follows (See FIG. 1A):

a.) A row 18 of control wells 14 containing only buffer dilutions and dye to establish the background color in the absence of either HD or the compound of interest (i.e., the compound to be assessed for its effect on HD solubility).

b.) A row 20 of control wells 14 containing only buffer dilutions, dye and HD to establish the spontaneous rate of HD hydrolysis in the absence of the compound of interest.

c.) A row 22 of control wells 14 containing buffer, dye and the compound of interest, but no HD. The purpose of this control was to observe and pH effects from the compound of interest in the absence of HD.

d.) A row(s) 24 of experimental wells 14 had the same content as in c.) above, plus 1% HD by weight. The difference in color change observed between (c.) above and the experimental wells could only be due to the effects resulting from the reaction of HD in the aqueous system.

One row 18 of wells 14 was designed as the control, to which only HD will be added. The results from this row 18 indicated the rate of HD hydrolysis in the absence of hydrolysis enhancing agents such as surfactants, catalysts or enzymes. Another control row 20 containing only buffer, dye and the potential hydrolysis enhancing agent or compound of interest, was used as a base control. This control indicated acid production from the compound of interest, in the absence of HD. The remaining rows 22, 24 were filled with buffer dilutions, dye, HD, and the compound of interest to be tested. HD was added to each appropriate well to a final effective concentration of 1% by weight and the plate 12 was placed on a microtiter plate shaker to ensure equivalent agitation to all the wells 14. As the HD hydrolyzed during the incubation, acid was released and the wells 14, in order of increasing buffer concentration, gradually turn color from purple to yellow to red. The relative rates of hydrolysis were determined by observing the number of wells 14 in a given row that changed color at an intermediate point in time (i.e. prior to the time of complete hydrolysis).

As an example for reading the plate 12, FIG. 2 shows a comparison of HD added neat in row 32 and HD added in row 30 as a 10% solution in isopropanol (the final effective concentration of HD was 1% in both cases). Clearly, the HD added as an isopropanol (IPA) solution hydrolyzed much more rapidly, as seen by the number of wells 14 with color change in 30 min.

The results shown in FIG. 2 confirmed what was already known from chloride electrode assays. The HD/IPA hydrolysis represented by row 30 proceeds significantly more rapidly than that of neat HD under the same conditions represented by row 32. Therefore, differential rates can be semi-quantitatively visualized in the colorimetric assay of the present invention based on the number of wells exhibiting color change in a given time period.

A series of detergents and other surfactants were tested in a similar manner. In all cases, their hydrolysis rates were compared directly to the rate of HD alone with no surfactant. Although some test compounds initially produced greater color change than the wells with HD alone, when control C) (above) was observed (i.e., buffer, dye, compound of interest, but no HD), it was clear that the pH change was caused primarily by the acidity of the test compound itself, not by HD hydrolysis. Of all the compounds tested, none were seen to clearly enhance the rate of HD hydrolysis, and most compounds significantly inhibited or reduced the rate of hydrolysis. This was essentially consistent with results reported from a previous study when a series of detergents were tested by chloride electrode assays.

FIG. 3 shows the results of a typical assay support 50 where all test compounds as represented by rows 52, 54, 56, 58, 60, 62 and 64, respectively, were added to a final concentration of 1%, and the assay support 50 was covered, and placed on the shaker (not shown) for a total of two hours prior to photography. Results show that HD alone as represented by row 66 (control, top row) hydrolyzed faster than HD in the presence of any of the test compounds.

The following is a list of compounds tested against HD in the Microtiter Plate Assay: 1% AFFF Class B Foam, 1% Class A 4 Knockdown, 1% Uni A Class A Foam, 1% XL-3 Fluoroprotein, 1% dodecylbenzene SA, 1% A4P 3/6 AFFF Alcohol-res, 1% PEG 400, 3% PEG400, 5% PEG400, 10% PEG400, 1% PEG200, 5% PEG200, 10% PEG200, 1% PEG dimethyl ether, 5% PEG dimethyl ether, 10% PEG dimethyl ether, 1% tetramethylene glycol, 5% tetramethylene glycol, 10% tetramethylene glycol, 1% thiodiglycol, 5% thiodiglycol, 10% thiodiglycol, 1% 1,4 butanediol, 1% Hexadecyl trimethylammonium bromide, 1% PEG 6000, 1% Bare Ground, 1% Dextran sulfate, 1% polyvinylpolypyrrolidone, 1% Tide Free, 2, 2 azino-bis(3-ethylbenzthiazoline-6-sulfonic acid) diammonium salt, 1% dioctyl sulfosuccinate sodium salt, 1% Dimethyl-dioctadecylammonium bromide, 1% Brij 56, 1% 1-dodecane sulfonic acid, 1% Dodecyl-beta-D-maltoside, 1% Thiodiglycolic acid, 1% Cetyltrimethyl ammonium chloride, 1% Lauric acid, 1% N-lauroylsarcosine sodium salt, 1% Triton type CF-54, 1% Glycine P.A., 1% Hexanediol, 1% TAPSO, 1% Petrogen surfactant, 5% Petrogen surfactant, 5% 1,4 butanediol, 10% 1,4 butanediol, 1% Universal Plus 3/6%, 1% Universal Gold 3%, 1% Aero-lite 3%, 1% Tween 20, 1% DDSAH, 1% lactic acid, 1% propylene glycol, 1% Aero-lite 3% cold foam, 1% Tween 80, 1% Triton N101, 1% 0.3% AFFF concentrate, 1% Glutathione, reduced acid water 3em, 1% Triton X100, reduced, 1% Aero-foam Cold Foam, 1% ethylene glycol, 1% benzalkonium chloride, 1% polyvinylpolypyrrolidone, 1% Brij 58, and 1% Benzyldimethyl tetradecyl ammonium chloride dihydrate.

Initial concentrations of test compounds were generally 1%. In cases where the results of the 1% tests were ambiguous, other concentrations were tested and/or compounds were tested in the chloride electrode assay. None of the compounds listed above were clearly observed to enhance the hydrolysis of HD under the conditions tested and the chloride electrode assay confirmed the finding of the assay of the present invention.

CONCLUSION

A colorimetric microtiter plate assay for one embodiment of the present invention was developed based on the pH differences resulting from HD hydrolysis at varying rates. The assay of the present invention was shown to provide a convenient, semi-quantitative means by which to compare HD hydrolysis rates under a series of different conditions. Results observed with the plate assay in the present invention were consistent with those from chloride electrode assays with the same materials. Using the plate assay of the present invention, a series of detergents and other surfactants were screened to determine their effect on the HD hydrolysis rate. None of the compounds tested were observed to enhance HD hydrolysis and most of the compounds significantly inhibited the reaction. The simplest explanation for the decreased hydrolysis rates observed in the presence of the detergents is probably that the detergent micelles sequestered the HD in a hydrophobic environment where they are not as susceptible to hydrolysis.

The forgoing discussion discloses and describes merely exemplary embodiments of the present invention. One skilled in the art will readily recognize from such discussion, and from the accompanying claims, that various changes, modifications, and variations can be made therein without departing from the spirit and scope of the invention as defined in the following claims. For example, the color changes in wells 14 can be read by a color detecting device which provides signals indicative of the color changes, whereby the device has greater sensitivity to color changes than the human eye. Such a device can be included in an automated system.

What is claimed is:

1. An assay kit for screening potential hydrolysis enhancing agents capable of enhancing the hydrolysis of a substantially water insoluble halogenated compound in an aqueous reaction mixture to form an acid, said assay kit comprising:
   at least one chamber containing a chemical warfare agent and a potential hydrolysis enhancing agent in an aqueous reaction mixture, wherein said potential hydrolysis enhancing agent is selected from the group consisting of catalysts, enzymes, surfactants, detergents, and combinations thereof; and
   an indicating agent comprising a pH indicator adapted to produce a color change corresponding to the amount of acid formed by hydrolysis of the chemical warfare agent in the aqueous reaction mixture, wherein the rate of hydrolysis can be established by measuring the color change over time.

2. The assay kit of claim 1, wherein the chemical warfare agent is a chlorine-containing compound.

3. The assay kit of claim 1, wherein the chemical warfare agent is HD.

4. The assay kit of claim 1, wherein the pH indicator is selected from the group consisting of meta-cresol purple, thymol blue and a universal pH indicator.

5. The assay kit of claim 1, wherein the at least one chamber is a plurality of chambers.

6. The assay kit of claim 5, wherein the plurality of chambers is disposed in a series of coextensive linear arrangements.

7. The assay kit of claim 6, wherein succeeding chambers of each linear arrangement are adapted to receive and retain an aqueous reaction mixture containing graduated concentrations of a buffer.

8. The assay kit of claim 7, wherein the chambers of one of said linear arrangements are adapted to receive and retain an aqueous reaction mixture containing only the buffer and the indicating agent.

9. The assay kit of claim 7, wherein the chambers of one of said linear arrangements are adapted to receive and retain an aqueous reaction mixture containing only the buffer, indicating agent, and the substantially water insoluble halogenated compound.

10. The assay kit of claim 7, wherein the chambers of one of said linear arrangements are adapted to receive and retain an aqueous reaction mixture containing only the buffer, the indicating agent, and a potential hydrolysis enhancing agent.

11. The assay kit of claim 7, wherein the chambers of one of said linear arrangements are adapted to receive and retain an aqueous reaction mixture containing only the buffer, the indicating agent, the substantially water insoluble halogenated compound, and a potential hydrolysis enhancing agent.

12. The assay kit of claim 6, wherein the plurality of chambers comprises a micro titer plate.

13. The assay kit of claim 1, wherein the at least one chamber comprises a plurality of chambers disposed in a series of coextensive linear arrangements and wherein a first set of chambers disposed in the series of coextensive linear arrangements is adapted to receive and retain a first aqueous control mixture containing an aqueous buffer solution and the pH indicator, wherein a second set of chambers disposed in the series of coextensive linear arrangements is adapted to receive and retain a second aqueous control mixture containing the aqueous buffer solution, the pH indicator and the chemical warfare agent, wherein a third set of chambers disposed in the series of coextensive linear arrangements is adapted to receive and retain a third aqueous control mixture containing the aqueous buffer solution, the pH indicator and the potential hydrolysis enhancing agent, wherein a fourth set of chambers disposed in the series of coextensive linear arrangements is adapted to receive and retain an aqueous test mixture containing the aqueous buffer solution, the pH indicator, the chemical warfare agent and the potential hydrolysis enhancing agent and wherein the rate of hydrolysis can be established by observing a color change produced by the pH indicator over a period of time for the fourth set of chambers that is different than any of the first, second and third sets of chambers.

14. The assay kit of claim 13, wherein the plurality of chambers comprises a micro titer plate.

15. An assay kit for screening potential hydrolysis enhancing agents capable of enhancing the hydrolysis of a chemical warfare agent in an aqueous mixture, said assay kit comprising:
   a plurality of chambers disposed in a series of coextensive linear arrangements, at least one chamber containing a chemical warfare agent and a potential hydrolysis enhancing agent, wherein the potential hydrolysis enhancing agent is selected from the group consisting of catalysts, enzymes, surfactants, detergents, and combinations thereof; and a pH indicator adapted to produce a color change corresponding to the amount of the chemical warfare agent hydrolyzed in the aqueous mixture, the pH indicator being selected from the group consisting of meta-cresol purple, thymol blue and a universal indicator;

wherein a first set of chambers disposed in the series of coextensive linear arrangements is adapted to receive and retain a first aqueous control mixture containing an aqueous buffer solution and the pH indicator, wherein a second set of chambers disposed in the series of coextensive linear arrangements is adapted to receive and retain a second aqueous control mixture containing the aqueous buffer solution, the pH indicator and the chemical warfare agent, wherein a third set of chambers disposed in the series of coextensive linear arrangements is adapted to receive and retain a third aqueous control mixture containing the aqueous buffer solution, the pH indicator and the potential hydrolysis enhancing agent, wherein a fourth set of chambers disposed in the series of coextensive linear arrangements is adapted to receive and retain an aqueous test mixture containing the aqueous buffer solution, the pH indicator, the chemical warfare agent and the potential hydrolysis enhancing agent and wherein the rate of hydrolysis can be established by observing a color change produced by the pH indicator over a period of time for the fourth set of chambers that is different than any of the first, second and third sets of chambers.

* * * * *